United States Patent [19]

Rupp et al.

[11] 4,096,738
[45] Jun. 27, 1978

[54] METHOD FOR TESTING FILLED GLASS CONTAINERS

[75] Inventors: Roland Rupp, Leverkusen; Hildegard Schnoring, Wuppertal; Erhard Schellmann, Cologne; Kurt Bauer, Leverkusen, all of Germany

[73] Assignee: Bayer Aktiengesellschaft, Leverkusen, Germany

[21] Appl. No.: 776,051

[22] Filed: Mar. 9, 1977

[30] Foreign Application Priority Data

Mar. 25, 1976 Germany .......................... 26128096

[51] Int. Cl.² ............................................. G01M 7/00
[52] U.S. Cl. .......................................... 73/52; 73/595
[58] Field of Search ................ 73/40, 52, 67, 69, 67.3, 73/577, 592, 595, 662

[56] References Cited

U.S. PATENT DOCUMENTS

| 2,339,460 | 1/1944 | Cozzoli | 73/52 |
| 2,859,610 | 11/1958 | Dickey | 73/69 |
| 3,541,838 | 11/1970 | Antonevich | 73/67 |

*Primary Examiner*—S. Clement Swisher
*Attorney, Agent, or Firm*—Burgess, Dinklage & Sprung

[57] ABSTRACT

The containers to be tested are brought into an ultrasonic wave field of which the intensity is assessed so that defective containers are destroyed, while mechanically perfect containers remain unaffected. Since the containers destroyed fall out of their holders, sorting takes place simultaneously.

8 Claims, 4 Drawing Figures

METHOD FOR TESTING FILLED GLASS CONTAINERS

The invention relates to a method for testing filled glass containers for leaks and mechanical strength. The method is particularly suitable for testing medical ampoules.

Containers for sterile medicine preparations (e.g. ampoules) must be free from leaks in order to protect the contents from contamination. In addition, the mechanical strength should not fall below certain limit values. Otherwise, safety from breakage in fully automatic packaging or in storage and dispatch would no longer be guaranteed. For this reason, subsequent to the filling and sealing of the container, a test for leaks and freedom from damage of the containers must be effected.

The hitherto known methods for testing medical ampoules for leaks are based on the penetration of dye solutions. The ampoules are introduced into a dye bath, so that the contents of defective ampoules are coloured by the dye bath at a specific pressure differential over a period of from 15 to 30 minutes. The ampoules treated in the dye bath are checked for discoloration after a washing process. The various variants of this dye bath method are for example described in "DPSC Standards for the Manufacture and Packaging of Drugs, Pharmaceuticals and Biological Products" and in "Methods of detecting leaks in glass ampoules", G. Brizell, J. Shatwell, Pharm. J. 1973 pages 73 to 74.

These methods have the disadvantage that the recognition of cracks in ampoules is incomplete and unsatisfactory. The cause is mainly that cracks in the glass initially shut tight and thus prevent the penetration of the dye solution. In addition, the dye baths must be frequently renewed. The dye baths thrown away constitute an environmental threat. Furthermore, there is the risk that only slightly discoloured ampoules are not recognised and separated. Such ampoules can constitute a danger of poisoning.

The object of the invention is to provide for the pharmaceutical industry a method for testing glass containers which permits rapid and reliable selection of defective containers. The crux of the problem is in the recognition of cracks and mechanical weak points.

According to the invention, there is provided a method for testing filled glass containers, in particular ampoules, for leaks and mechanical strength, wherein the containers are brought into an ultrasonic wave field, produced by an ultrasonic source of which the intensity is such that defective containers are destroyed, while mechanically perfect containers remain unaffected.

For this purpose the containers may be guided successively past an ultrasonic source. The ultrasonic source can be coupled to the containers either directly or by means of a liquid, e.g. water. For testing medical ampoules an ultrasonic generator having a frequency of approximately 20 kHz and a rating in the region of 600 to 1500 W is preferably used. In this arrangement the ultrasonic generator is advantageously pressed against the container with a force of from 1 to 6 N, preferably 1.4 to 2 N.

The method according to the invention has the advantage that it does not require any dye baths and is easy to carry out. The reliability of defect recognition is 95 to 100%. As the defective containers are destroyed, they can be easily separated. This principle permits the construction of a relatively simple and economical monitoring station.

Figure 1:
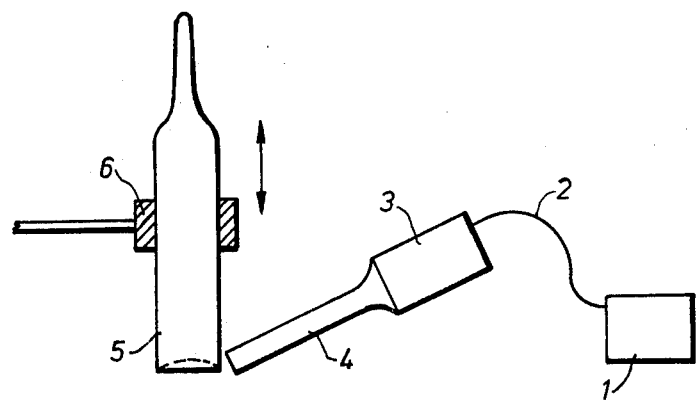
FIG. 1 shows schematically a test apparatus for carrying out the method according to the invention.

The ultrasonic wave field for testing ampoules is produced according to FIG. 1 by an ultrasonic generator 1. It has a frequency of 20 kHz and a rating of 700 W. The electrical power is transmitted by a cable 2 to an ultrasonic resonator 3, e.g. a quartz resonator, which has a nozzle 4 for radiating the ultrasonic energy. The nozzle 4 is either connected directly or indirectly via a fluid to an ampoule 5 to be tested which is held in a rubber sleeve 6. The ampoule 5 is made to oscillate in the axial or radial direction.

Figure 2:
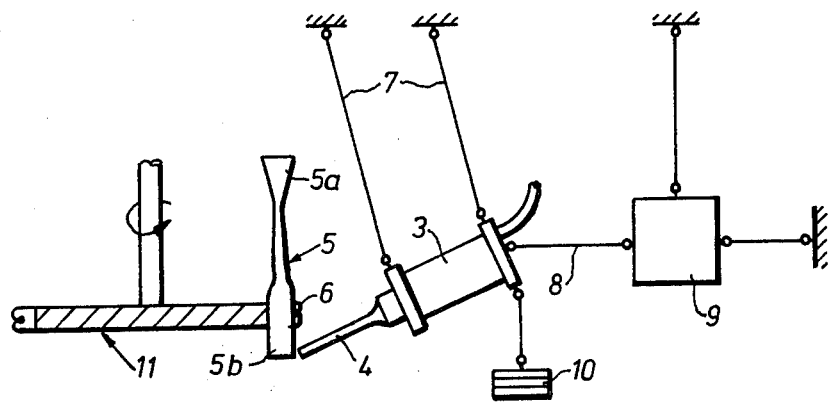
FIG. 2 shows an experimental apparatus for the ultrasonic testing of ampoules.

The arrangement shown in FIG. 2 permits the measurement of the relevant data for the ampoule test. The ultrasonic resonator 3 is suspended on wires 7. Because of lateral guides and a retaining wire 8 with an interconnected force recorder 9, the ultrasonic transmitter 3 can only swing backwards. This design enables the ampoule 5 to be loaded with horizontal forces of a maximum of 10 N by attaching additional weights 10.

The ampoules 5 are supported by means of rubber rings 6 in a rotary plate 11. The ultrasonic resonator 3 with the nozzle 4 does not alter its position on contacting the ampoule 5. This is achieved by means of a sprung support of the rotary plate 11. The contact force of the nozzle 4 on the ampoule 5 is measured by the inductive force recorder 9 and the equivalent output voltage is supplied to one channel of a two channel X - T recorder. The second channel of the recorder is fed with a direct voltage proportional to the power consumption of the ultrasonic resonator. The sonic exposure time is also measured in addition to the contact force and power delivery of the resonator.

When the nozzle 4 contacts the ampoule 5, a true power is transmitted to the ampoule. It is not dependent on the pressure force and increases strongly at the beginning of breakage. No resonance is achieved between the resonator 3 and ampoule 5.

It has been found that the contact force is of importance in the recognition of different defect points. Thus for the recognition of cracks in the ampoule tip 5a, other contact forces are necessary than for the recognition of cracks in the ampoule base 5b. To recognise cracks in the tip it is best to work with a contact force in the range 1.4 to 2 N, whereas for the recognition of base cracks, it is useful to work in the range 5 to 6N.

Figure 3A:
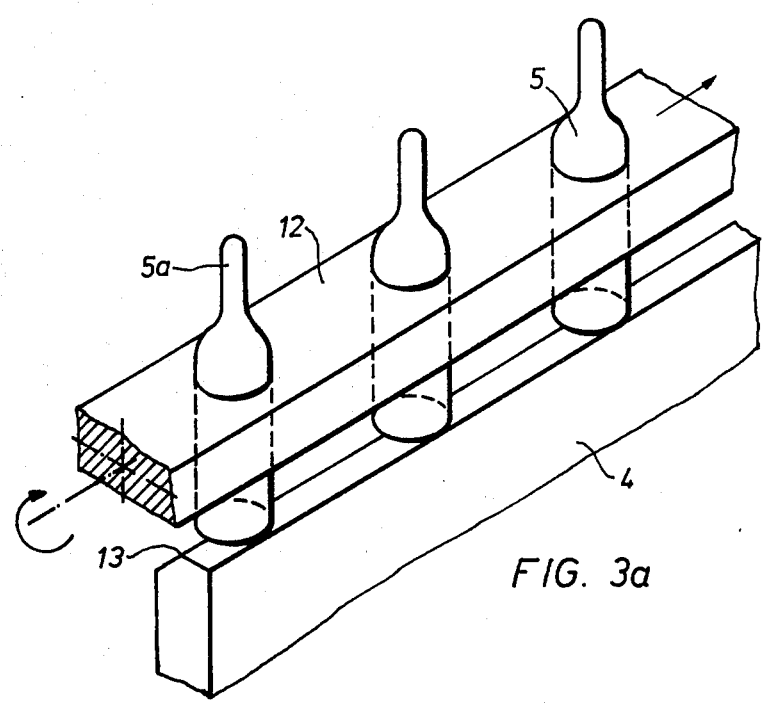
FIG. 3a shows an ampoule holder for testing for base and tip cracks.

As shown in FIG. 3a, when testing for base or tip cracks, the ampoules 5 are exposed to sonic radiation in the direction of the ampoule axis. In the embodiment according to FIG. 3a the ampoule holder is in the form of a rectangular bar 12, into which the ampoules 5 are inserted at regular intervals. The ultrasonic nozzle 4 has a sharp edge 13 and is of a length such that up to 10 ampoules can be simultaneously exposed to sonic radiation. In continuous operation the ampoules 5 are moved by uniform advance of the holder 12 over the edge 13 of the ultrasonic nozzle 4. The rate of advance is adjusted so that the ampoules remain in contact with the nozzle and are exposed to sonic radiation for several seconds.

The holder 12 is in addition pivoltable through 90° about an axis perpendicular to the ampoule axis. In this way either the base 5b or the tip 5a of the ampoules can be brought into contact with the ultrasonic nozzle 4.

Figure 3B:
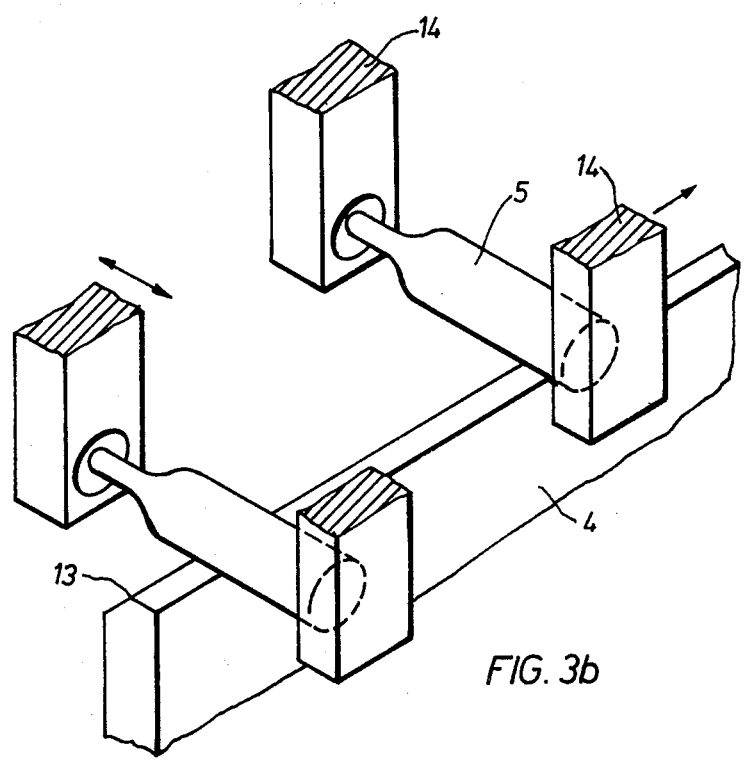
FIG. 3b shows an ampoule holder for testing for body cracks.

FIG. 3b shows schematically an ampoule holder 5 which permits continuous testing for body cracks. The ampoules 5 are here held by the base and tip, so that the ampoule body remains free. The ultrasonic nozzle 4 again has a knife edge 13. The ampoule holder 14 can be moved perpendicular to the ultrasonic nozzle edge 13 so that the edge 13 passes over the ampoule body during testing. At the same time the ampoule holder 14 executes a feed movement parallel to the ultrasonic nozzle edge 13. The ampoule holder can be constructed so that the ampoules rotate about their longitudinal axis.

In the two embodiments shown in FIGS. 3a and 3b, the ultrasonic coupling can be improved by spraying water in the contact zone of the nozzle 4. In both cases defective ampoules are destroyed and drop from the holder 12 or 14. For this reason no additional sorting devices are required.

EXAMPLE 1

Filled 2 ml ampoules with cracks in the tip were brought into contact with the nozzle 4 of an ultrasonic resonator (frequency 20 kHz, rating 700 W) for a period of 2 seconds by using the device according to FIG. 2. The contact force was 1.4 N, the direction of force was radial to the ampoule axis. No fluid was used as a coupling medium. The selection rate for damaged ampoules was 100%.

EXAMPLE 2

Filled 2 ml ampoules with tip cracks were guided under water past the nozzle 4 of an ultrasonic resonator 3 (frequency 20 kHz rating 1300 W) without contact. The distance between the nozzle tip and the ampoule was approximately 0.5 ml, the selection rate 100%.

What we claim is:

1. A method for testing filled glass containers in particular, ampoules for leaks and mechanical strength, comprising bringing the containers into an ultrasonic wave field produced by an ultrasonic source, without impact between the containers and the source and setting the intensity of the ultrasonic source to intensity at a predetermined frequency to destroy defective containers, while mechanically perfect containers remain unaffected.

2. A method as claimed in claim 1, wherein the containers are guided successively past the ultrasonic source.

3. A method as claimed in claim 1, wherein the ultrasonic source is coupled directly to the container.

4. A method as claimed in claim 1, wherein the ultrasonic source is indirectly coupled to each container via a fluid.

5. A method as claimed in claim 1, wherein the ultrasonic source is an ultrasonic generator having an intensity in the range of from 600 to 1500 W.

6. A method as claimed in claim 5, wherein the ultrasonic generator is pressed against the container with a force of from 1 to 6 N.

7. A method as claimed in claim 6, wherein the ultrasonic generator is pressed against the container with a force of from 1.4 to 2 N.

8. A method according to claim 5, wherein the ultrasonic generator has a frequency of approximately 20 kHz.

* * * * *